US012626800B2

(12) United States Patent
Koplin et al.

(10) Patent No.: US 12,626,800 B2
(45) Date of Patent: May 12, 2026

(54) TELEMETRIC DOSAGE CONTROLLER SYSTEM

(71) Applicant: Eye Thena, Inc., New York, NY (US)

(72) Inventors: Richard S. Koplin, New York, NY (US); Kari Thorstensen, New York, NY (US); Geoff Scott, Williston Park, NY (US)

(73) Assignee: EyeThena, Inc., New York, NY (US)

( * ) Notice: Subject to any disclaimer, the term of this patent is extended or adjusted under 35 U.S.C. 154(b) by 0 days.

(21) Appl. No.: 19/355,481

(22) Filed: Oct. 10, 2025

(65) Prior Publication Data

US 2026/0106011 A1 Apr. 16, 2026

Related U.S. Application Data

(60) Provisional application No. 63/706,168, filed on Oct. 11, 2024.

(51) Int. Cl.
| | |
|---|---|
| *G16H 20/10* | (2018.01) |
| *A61J 1/18* | (2023.01) |
| *A61J 7/04* | (2006.01) |
| *G16H 10/60* | (2018.01) |
| *G16H 40/67* | (2018.01) |

(52) U.S. Cl.
CPC ............... *G16H 20/10* (2018.01); *A61J 1/18* (2013.01); *A61J 7/0418* (2015.05); *A61J 7/0436* (2015.05); *G16H 10/60* (2018.01); *G16H 40/67* (2018.01); *A61J 2200/30* (2013.01)

(58) Field of Classification Search
CPC ........ G16H 20/10; G16H 10/60; G16H 40/67; A61J 1/18; A61J 7/0418; A61J 7/0436; A61J 2200/30
See application file for complete search history.

(56) References Cited

U.S. PATENT DOCUMENTS

| | | | | |
|---|---|---|---|---|
| 9,378,531 | B2 * | 6/2016 | Pecora | ............... G06Q 10/0637 |
| 11,468,993 | B2 * | 10/2022 | Koplin | ................... G16H 10/40 |
| 11,547,499 | B2 * | 1/2023 | Geri | ........................ A61B 34/20 |
| 11,640,858 | B2 * | 5/2023 | Koplin | ................... G16H 20/00 |
| | | | | 705/2 |
| 12,488,897 | B2 * | 12/2025 | Koplin | ................... G16H 10/60 |

(Continued)

*Primary Examiner* — Michael Collins
(74) *Attorney, Agent, or Firm* — Baker & McKenzie LLP

(57) ABSTRACT

The disclosed telemetric control system comprises: at least one activatable member configured to be actuated upon administration of a medication thereby triggering an actuation event of the system that initiates electronic tracking of a medication administration event; a signal transmitter operatively coupled to the at least one activatable member and which is configured to transmit or receive data signals via at least one wireless network; one or more non-transitory memory devices storing control logic customized to the identifier data associated with the electronic health record of the first biological system; and a powering mechanism configured to supply energy to components of the telemetric control system. It is appreciated that actuating the at least one activatable member triggers the signal transmitter to securely transmit encrypted data to a server for substantially real-time monitoring, automated alert generation, and adherence management associated with at least a medication.

20 Claims, 4 Drawing Sheets

(56)                    References Cited

U.S. PATENT DOCUMENTS

| | | | |
|---|---|---|---|
| 2015/0149212 A1* | 5/2015 | Rolia ..................... | G16H 50/20<br>705/3 |
| 2022/0139519 A1* | 5/2022 | Schilling ............... | G16H 15/00<br>705/2 |

* cited by examiner

404

402

TELEMETRIC
DOSAGE
CONTROLLER SYSTEM
110a

406

402

TELEMETRIC DOSAGE
CONTROLLER SYSTEM
110b

408

402

TELEMETRIC DOSAGE
CONTROLLER SYSTEM
110c

TELEMETRIC DOSAGE CONTROLLER SYSTEM

CROSS-REFERENCE TO RELATED APPLICATIONS

This application claims priority to, and benefit of U.S. Provisional Patent App. No. 63/706,168, filed on Oct. 11, 2024, and titled "Medication Tracking Device," which is incorporated herein by reference in its entirety for all purposes.

FIELD OF DISCLOSURE

The present disclosure is directed to a telemetric system for managing medication delivery to biological systems.

BACKGROUND

There is a need for systems and methods that track, monitor, and inform the delivery of medications to biological systems.

SUMMARY

The disclosed telemetric control system is configured for improving medication adherence through substantially real-time dosage tracking and medication delivery management. According to one embodiment, the telemetric control system comprises: at least one activatable member configured to be actuated upon administration of a first medication thereby triggering an actuation event of the system that initiates electronic tracking of a medication administration event associated with the first medication. It is appreciated that the medication administration event represents a delivery of the first medication to a first biological system (e.g., a patient).

The telemetric control system can also include a signal transmitter operatively coupled to the at least one activatable member and which is configured to transmit or receive data signals via at least one wireless network. According to one embodiment, the signal transmitter relays one or more of: timestamp data associated with the actuation event; dosage verification data associated with the first medication; and identifier data associated with an electronic health record (EHR) of the first biological system.

The telemetric control system can also comprise one or more non-transitory memory devices storing control logic customized to the identifier data associated with the electronic health record of the first biological system. In one embodiment, customizing the control logic to identifier data associated with the EHR involves adapting the telemetric control system's control logic and operational parameters to the attributes of a specific biological system, as identified by data such as the name of the biological system, medical record information of the biological system, or other identifiers within the EHR. This customization ensures that the telemetric control system's functions—such as tracking medication administration events, correlating dosage parameters, and adjusting delivery schedules—are personalized to the specific medical profile of the biological system, including their prescribed medications, health conditions, and treatment plans. For instance, the control logic may map actuation events to the patient's drug type, dosage quanta, and delivery intervals as recorded in the EHR, while also integrating physiological feedback or patient-reported outcomes specific to that biological system. By leveraging identifier data, the telemetric control system ensures accurate, patient-specific monitoring and management, enhancing medication adherence and minimizing risks in complex scenarios like polypharmacy, while maintaining compliance with healthcare standards.

According to one embodiment, the control logic is configured to: correlate or map the actuation event with dosage parameters including: a drug type parameter associated with the first medication; dosage quanta data associated with delivery of the first medication to the first biological system; and delivery interval data associated with a first temporal window between a first delivery of the first medication to the first biological system, and a second delivery of the first medication to the first biological system; and dynamically adjusting the dosage parameters based on physiological or biomarker data associated with delivery of the first medication to the first biological system, or a second medication. Dynamically adjusting the dosage parameters can also be based on response data associated with: a first detected effect of the first medication on the first biological system; a second detected effect of a second medication on the first biological system; or a third detected effect of a third medication on the first biological system or a second biological system.

The disclosed telemetric control system comprises a powering mechanism configured to supply energy to components of the telemetric control system, the powering mechanism including at least one of: a rechargeable battery system coupled to, or integrated into the telemetric control system; a disposable battery system configured to power the telemetric control system for a second temporal window; a wireless charging energy system configured to wirelessly charge or power the telemetric control system; or an energy harvesting system configured to use kinetic energy, thermoelectric energy, or vibrational energy associated with the first biological system.

It is appreciated that actuating the at least one activatable member triggers the signal transmitter of the telemetric control system to securely transmit encrypted data to a server for substantially real-time monitoring, automated alert generation, and adherence management associated with at least the first medication.

These and other implementations may each optionally include one or more of the following features.

The at least one activatable member can comprise a button or touch-sensitive interface directly coupled to a medication container or positioned proximal thereto. This coupling can be achieved via an adjustable band configured to fit around varying container diameters including a first diameter of a container within which is the first medication. The adjustable band can be an elastic band according to some embodiments.

In some embodiments, the at least one activatable member is coupled to a medication container via, for example, an elastic band fabricated from silicone or latex-free materials, the elastic band being structured to: stretch and thereby conform to a container contour of a container within which is placed the first medication; and incorporate an anti-slip texture for stabilizing the elastic band around the container. In other embodiments, the at least one activatable member is coupled to a medication container via a Velcro-based fastening system comprising hook-and-loop strips, allowing reusable and repositionable attachment with or without magnetic assistance for one-handed operation of the telemetric control system.

In some cases, the activatable member of the telemetric control system is coupled via adhesive means, such as pressure-sensitive adhesives or medical-grade epoxies with residue-free removal, combined with tamper-detection sensors to alert the control logic stored in the one or more non-transitory memory devices, of unauthorized removal attempts.

Furthermore, the control logic is further configured to generate, or initiate generations of a multidimensional report including: medication adherence data associated with delivering to the first biological system, the first medication or the second medication; pharmacokinetic adherence curve data indicating an assessment or prediction of how closely a medication regimen of the first medication or the second medication is observed by the first biological system; and predictive analytics data based on historical actuation patterns of the at least the one activatable member.

According to one embodiment, the multidimensional report comprises multi-modal data including visual timelines, interactive charts, and audio summaries. The multidimensional report can comprise: a timestamp data of delivering at least the first medication to the first biological system within the first temporal window, the second temporal window, or a third temporal window; dosage quanta data associated with delivering the first medication to the first biological system during the first temporal window, the second temporal window, or the third temporal window; and deviation data associated with inconsistent delivery of the first medication to the first biological system over the first temporal window, the second temporal window, or the third temporal window.

In some cases, the multidimensional report referenced above is configured or structured to be visualized on a display computing device in one of a Portable Document Format (PDF) file format, a Comma-Separated Values (CSV) file format, a data format associated with textual data, video data, or audiovisual data.

According to one embodiment, the telemetric control system further comprises an interface for bidirectional integration with an EHR system that is compliant with a Health Level Seven International (HL7) Fast Healthcare Interoperability Resources (FHIR) standards. Furthermore, the multidimensional report can comprise: cumulative adherence rate data indicating delivering at least the first medication to the first biological system; anomaly detection data indicating unexpected dosage variations associated with delivering at least the first medication to the first biological system; and machine learning-based risk prediction data associated with optimizing delivery of at least the first medication to the first biological system.

In some embodiments, the multidimensional report includes a substantially real-time inventory depletion forecast generated, based on actuating the at least one activatable member. The inventory depletion forecast can indicate one or more of: a time for replenishing the first medication; and a quantity of the first medication to be replenished.

According to one embodiment, the telemetric control system further comprises one or more sensor arrays interfaced with the signal transmitter for acquiring physiological data of the first biological system such as biomarker levels or vital signs of the first biological system, enabling a closed-loop feedback mechanism that informs the control logic to dynamically adjust dosage quanta or delivery intervals of delivering the first medication to the first biological system.

In some instances, the telemetric control system is configured to facilitate remote prescription submission by automatically triggering refill requests to a linked pharmacy or an EHR system based on activating the at least one activatable member.

Moreover, the signal transmitter referenced in conjunction with the disclosed telemetric control system supports over-the-air (OTA) firmware updates to the one or more non-transitory memory devices of the telemetric control system and transmission of user-specific feedback, including aggregated actuation logs and adherence metrics, to healthcare providers for adjusting a medication regimen of the first medication relative to the first biological system.

In some cases, the telemetric control system comprises: a first activatable member of the at least one activatable member which is activatable to track the first medication; a second activatable member of the at least one activatable member which is activatable to track the second medication; and a third activatable member of the at least one activatable member which is activatable to track a third medication.

In some embodiments, the powering mechanism discussed above in association with the telemetric control system comprises a rechargeable lithium-ion battery with USB charging via a USB-A or micro-USB port, including a power management module that regulates charging cycles and optimize energy distribution for low-power operations between actuations of the at least one activatable member.

Furthermore, the powering mechanism can comprise a USB-C port supporting Power Delivery (PD) standards for faster charging and simultaneous data transfer during firmware updates or EHR synchronization.

In addition, the disposable battery system of the powering mechanism can comprise one of a coin-cell or alkaline battery, coin cel or alkaline battery, each of which can be housed in an accessible compartment of the telemetric control system and optimized for ultra-low power consumption through power saving modes that deactivate non-essential components from drawing energy from the powering mechanism during non-medication delivery times associated with the first medication.

In some embodiments the wireless charging energy system of the powering mechanism associated with the telemetric control system comprises wireless charging via a Qi-standard inductive charging with an embedded coil, allowing cable-free energy transfer to the telemetric control system and supporting sealed, water-resistant designs of the telemetric control system for enhanced durability in clinical or non critical environments.

According to one embodiment, the energy harvesting system referenced herein is configured to generate energy for the telemetric control system based on one or more: a piezoelectric generator embedded in the at least one activatable member, such that the piezoelectric generator converts mechanical energy from actuations of the at least one activatable member into electrical energy that powers the telemetric control system; or a photovoltaic cell for capturing and converting ambient light into electrical energy that powers the telemetric control system.

In one embodiment, the powering mechanism comprises a hybrid system with a primary rechargeable battery and a secondary disposable battery for failover, the control logic being configured to monitor battery levels and switching energy sources to maintain uninterrupted operation of the telemetric control system during power disruptions.

In some embodiments, the disclosed telemetric control system is configured for interoperability with Internet of Things (IoT) ecosystems, such that the signal transmitter communicates with external devices to contextualize dosage decisions based on environmental data, and blockchain technology for immutable logging of actuation events to ensure tamper-proof audit trails.

According to one embodiment, the at least one wireless network associated with the at least one wireless network is selected from the group consisting a Bluetooth Low Energy (BTLE) network, a Wi-Fi network, a satellite communications network, or a cellular network.

BRIEF DESCRIPTION OF THE DRAWINGS

This disclosure is illustrated by way of example, and not by way of limitation in the figures of the accompanying drawings in which like reference numerals are used to refer to similar elements. It is emphasized that various features may not be drawn to scale and the dimensions of various features may be arbitrarily increased or reduced for clarity of discussion.

DETAILED DESCRIPTION

Figure 1:
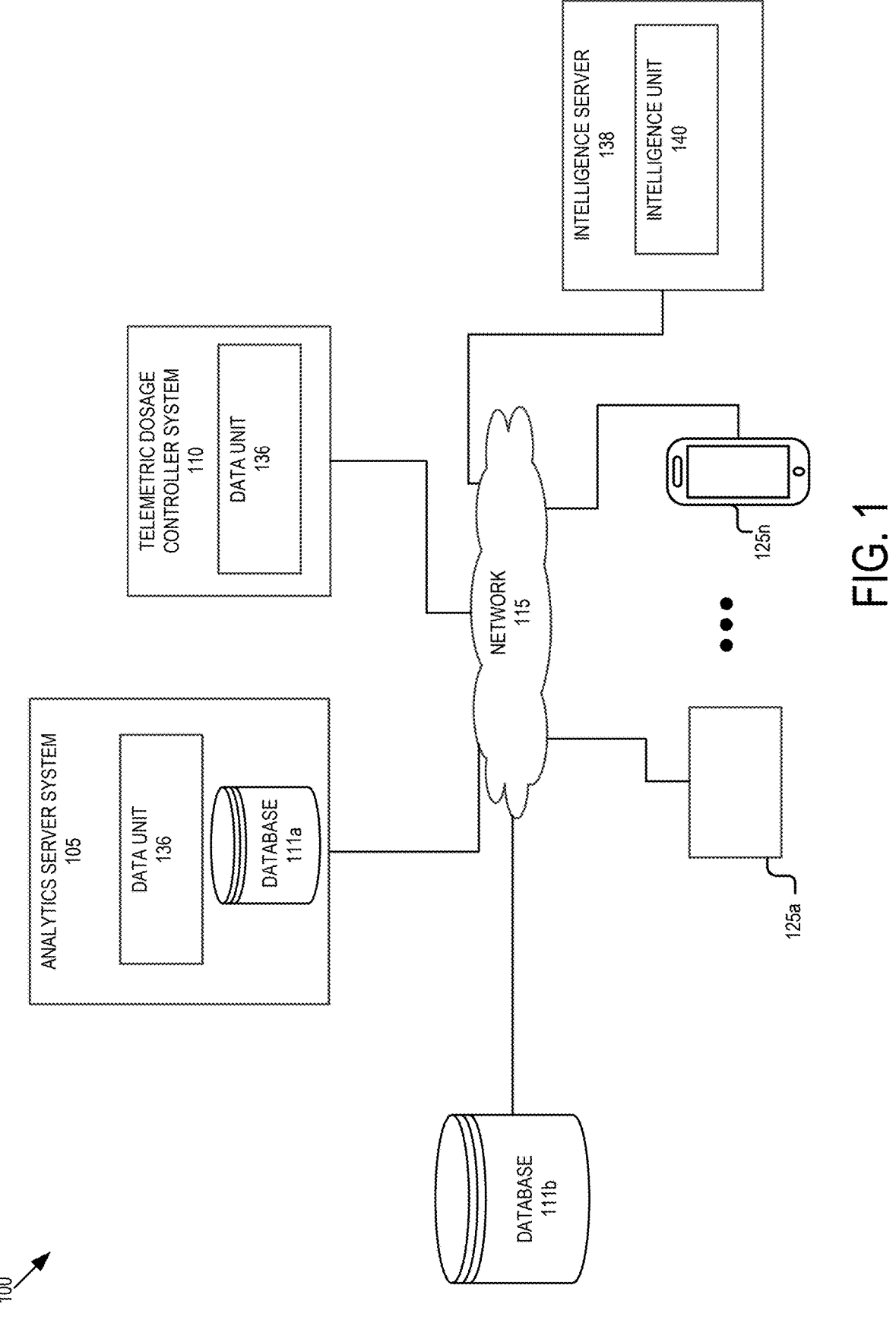
FIG. 1 shows an exemplary network system for executing the principles disclosed.

Reference will now be made in detail to embodiments, examples of which are illustrated in the accompanying drawings and figures. In the following detailed description, numerous specific details are set forth in order to provide a thorough understanding of the disclosed subject-matter. However, it will be apparent to one of ordinary skill in the art that the methods and systems disclosed may be practiced without these specific details.

As used herein, the term "exemplary" or "illustrative" means "serving as an example, an instance, or an illustration." Any implementation described herein as exemplary or illustrative is not necessarily to be construed as advantageous and/or preferred over other embodiments. Unless the context requires otherwise, throughout the description and the claims, the word "comprise" and variations thereof, such as "comprises" and "comprising" are to be construed in an open, inclusive sense, i.e., as "including, but not limited to."

Furthermore, the terms substantially real-time and near real-time, as used herein, refer to a processing and response timeframe that is close to, but not necessarily equal to, instantaneous or true real-time. While true real-time implies a delay of zero, any practical digital system will have some inherent latency due to data processing, computation, and network transmission. Therefore, these terms describe a timeframe where this inherent latency is sufficiently short as to be negligible for the effective operation of a given process or for the perception of a human user. The specific duration considered to be substantially real-time or near real-time is application-dependent and is defined by the requirements of the system to function as intended without being materially compromised by the delay.

Contextual Framework

Medication adherence is critical to preventing the progression of chronic diseases. In particular, it is needful for patients, especially those prescribed with more than one medication and as such may require technological systems that enable timely receiving, taking, and managing medication doses. For example, a glaucoma patient's medication may include eye drops, tablet medication, capsule medication, topical ointments, etc.

In some cases, patients may either lack technological savviness to navigate medication reception, delivery, and intake tracking. In particular, such a tracking through applications is an additional layer of complexity which most patients try to avoid.

In one embodiment, the disclosed telemetric dosage controller system (also simply referred to herein as telemetric control system) for dosage control and delivery incorporates an actuatable member, such as a button or switch, configured to initiate tracking upon manual or automated actuation coincident with medication administration. This actuatable member may be integrally formed with a medication container, such as a pill bottle cap, syringe housing, or inhaler body, wherein depression of the button triggers a time-stamped event log stored in an onboard memory device. Alternative implementations could position the actuatable member proximally to the container, for instance, as a wearable accessory like a smartwatch interface or an adhesive patch affixed to a vial, allowing seamless actuation without direct container modification. Further variations might employ touch-sensitive capacitive buttons for hygienic, contactless operation in clinical environments, or voice-activated equivalents integrated with natural language processing to accommodate users with motor impairments. Such multifaceted implementations ensure the system's adaptability to diverse medication formats, from oral tablets to injectable biologics, thereby facilitating precise adherence tracking.

It is appreciated that actuation of the actuatable member activates a signal transmitter, embodied as a wireless transceiver, to propagate data signals across one or more heterogeneous networks including Bluetooth Low Energy (BTLE) for low-power, short-range pairings with smartphones; Wi-Fi for broadband uploads to home gateways; satellite links for remote telemetry in off-grid locales; or cellular protocols like 5G for ubiquitous connectivity. In exemplary configurations, the transmitter relays actuation metadata—encompassing timestamp, dosage verification, and user identity—to a remote server or healthcare provider's dashboard. Embodiments may further integrate near-field communication (NFC) tags on the actuatable member, enabling tap-based interactions with compatible devices for supplemental data exchange, such as scanning a QR code on the container to cross-verify drug authenticity. These implementation modalities underscore the system's robustness, supporting real-time synchronization in both consumer and professional healthcare settings.

The telemetric dosage controller system further comprises one or more memory devices including control logic customized to a user profile, wherein the logic correlates or maps actuation events (e.g., actuation of the activatable member) with data parameters like drug type, dosage quanta, and scheduled delivery intervals. In some embodiments, the terms "drug type," "dosage quanta," and "scheduled delivery intervals" refer to specific data parameters associated with the disclosed system's operation and customization for user-specific medication management. Below, each term is defined as follows:

Drug Type: This data parameter refers to the specific identity and classification of a pharmaceutical agent(s) associated with the telemetric dosage controller system for a given user. It can encompasses data such as the chemical or generic name of the medication (e.g., metformin, insulin, or albuterol), its therapeutic class (e.g., antidiabetic, bronchodilator, or anticoagulant), and formulation characteristics (e.g., oral tablet, injectable solution, or inhaled powder). The drug type may also include metadata like mechanism of action, contraindications, or potential drug-drug interactions, enabling the control logic to tailor actuation events and monitoring protocols. For example, the system might differentiate between time-sensitive insulin and non-time-critical statins to prioritize alerts or actuation validations, ensuring compatibility with the biological system's therapeutic regimen.

Dosage Quanta: This term denotes the discrete, quantifiable units of medication prescribed for administration to the biological system (e.g., a patient), as determined by a healthcare provider and stored within the system's memory. Dosage quanta can specify the exact amount of the drug to be delivered per actuation event, expressed in units such as milligrams, milliliters, or puffs (for inhalers). This parameter may also account for variable dosing schedules, such as titration regimens where the quantity adjusts over time, or weight-based dosing calculated from biological system (e.g., a patient) profile data (e.g., body mass). For instance, the telemetric dosage controller system might log an actuation corresponding to a 10 mg dose of a drug, verifying it against the prescribed quanta to flag discrepancies, thereby enhancing precision in delivery and adherence tracking.

Scheduled Delivery Intervals: This parameter defines the temporal framework governing when medication doses should be administered, as encoded in the system's control logic. It can include specific times or time windows for actuation events (e.g., 8:00 AM daily, every 6 hours, or as needed within a 24-hour period), aligned with the pharmacokinetic and pharmacodynamic properties of the drug and the biological system's lifestyle or medical needs. The intervals may incorporate fixed schedules, dynamic adjustments based on real-time physiological feedback (e.g., from integrated biosensors), or conditional triggers, such as "post-meal" for certain antidiabetics. The system uses this parameter to prompt actuations, send reminders via the signal transmitter, or alert providers to deviations, ensuring timely and consistent medication delivery.

These data parameters collectively can enable the telemetric dosage controller system to operate with high specificity, aligning actuation events (e.g., actuation of the activatable member) with the biological system's prescribed regimen while supporting real-time monitoring, automated adjustments, and remote communication with healthcare providers. By integrating these parameters, the disclosed system ensures that medication administration is both accurate and personalized, optimizing therapeutic outcomes and biological system (e.g., a patient) compliance.

Advantages of incorporating the actuable button within the telemetric dosage controller system are manifold, prominently including heightened biological system (e.g., a patient) engagement and adherence through tactile feedback mechanisms, such as haptic vibrations or LED confirmations upon actuation, reinforcing behavioral compliance. By democratizing tracking—requiring minimal technical acumen—the system mitigates common barriers like forgetfulness or regimen complexity, potentially reducing hospitalization rates associated with non-adherence in chronic conditions like diabetes or hypertension or glaucoma. Moreover, the proximal or integrated button design minimizes workflow disruptions, allowing instantaneous logging during administration, which outperforms retrospective manual entries prone to errors or omissions. In aggregate, these benefits translate to optimizations for healthcare systems via preempted complications and optimized resource allocation.

In aspects pertaining to user or biological system data communication, the disclosed telemetric dosage controller system facilitates remote prescription submission triggered by quantitative assessments of remaining drug quantities in the container. Embodiments may enable the signal transmitter, based on the number of actuations of the activatable member, to autonomously relays a refill request to a linked pharmacy or electronic health record (EHR) system. This seamless integration obviates manual reordering, ensuring uninterrupted therapy continuity while empowering providers with predictive supply chain insights. Related implementations could employ machine vision via an affiliated app to scan container levels, further automating the process for some variants of the disclosed system.

Firmware updating constitutes another pivotal communication facet, wherein the telemetric dosage controller system supports secure OTA transmissions to refresh control logic, patch vulnerabilities, or incorporate new drug profiles without hardware replacement. Upon detection of available updates—perhaps via periodic polling through the cellular or Wi-Fi transmitter—the system queues installations during low-activity periods, minimizing user disruption. Advantages herein include prolonged device lifecycle and adaptability to evolving regulatory standards or pharmacological advancements, such as integrating support for novel biosimilars. In tandem, the system transmits user-specific feedback to healthcare providers, encompassing aggregated actuation logs, adherence metrics, and physiological correlates if biosensors are co-deployed, enabling data-driven consultations and personalized regimen adjustments.

It is contemplated that the telemetric dosage controller system may incorporate redundant communication pathways, such as fallback to SMS alerts via cellular networks if primary Wi-Fi fails, safeguarding critical data transmission during outages. Advantages include enhanced reliability in emergency scenarios, where timely provider notifications could avert adverse events like opioid overdoses through actuation-triggered overdose reversal protocols. Additionally, by aggregating anonymized data across biological system cohorts, the system supports epidemiological research, yielding insights into population-level adherence trends without compromising individual privacy.

In some embodiments, the actuatable member could interface with augmented reality (AR) overlays via companion apps, guiding users through administration steps prior to actuation, thereby reducing errors in complex delivery methods like subcutaneous injections. This educational augmentation, coupled with gamification elements—such as streak rewards for consistent actuations—fosters long-term behavioral change. Relatedly, the system's data communication framework might enable bidirectional feedback loops, where providers remotely reprogram dosage schedules based on transmitted metrics, closing the gap between prescription and real-world execution.

Overall, the disclosed telemetric dosage controller system's amalgamation of actuatable tracking, versatile implementations, and sophisticated data communications positions it as a cornerstone in precision medicine. By addressing unmet needs in adherence monitoring and proactive care, it not only amplifies therapeutic outcomes but also alleviates systemic burdens, paving the way for scalable, patient-empowered healthcare paradigms.

In one embodiment, the disclosed telemetric dosage controller system assigns a distinct activatable member, such as a dedicated button or touch-sensitive interface, to each individual medication within a user's prescribed regimen, thereby enabling granular tracking of multi-drug administration. For instance, in a modular container assembly, each medication vial or dispenser—such as one for antihypertensive pills, another for antidiabetic injections, and a third for anti-inflammatory creams—incorporates its own uniquely identifiable button, which may be color-coded, labeled with drug-specific icons, or embedded with haptic patterns for tactile differentiation. Upon actuation of a specific button during or immediately following medication delivery, the system logs the event via an integrated signal transmitter, correlating it with predefined data parameters like the corresponding drug type, dosage quanta, and scheduled delivery intervals stored in the device's memory. Alternative implementations could feature a centralized hub device, such as a smart pill organizer or wearable controller, where multiple buttons are arrayed in a user-configurable layout, each wirelessly paired to a remote sensor on the respective medication container; this allows for proximity-based actuation verification, ensuring the button press aligns with the physical removal or dispensing of the correct drug. Further variations might employ voice-activated or gesture-responsive buttons for hands-free operation, with the control logic employing machine learning to disambiguate inputs based on contextual cues like time of day or user biometrics.

Advantages of this per-medication button assignment are multifaceted, particularly in enhancing precision and safety for users managing polypharmacy, where multiple medications increase the risk of errors such as dose duplication or omission. By isolating tracking to individual drugs, the system facilitates independent adherence monitoring, allowing the control logic to generate targeted alerts-such as vibrations or notifications specific to a missed antihypertensive dose-without conflating regimens, thereby reducing cognitive load on users with complex schedules. This implementation also supports advanced data analytics, where multi-dimensional reports can delineate adherence patterns per drug, enabling healthcare providers to identify regimen-specific issues (e.g., poor compliance with evening medications due to fatigue) and tailor interventions accordingly. Moreover, in scenarios involving shared household devices or caregiver oversight, distinct buttons mitigate cross-user confusion, ensuring accurate attribution of actuations to the intended patient, which is especially beneficial in pediatric or elderly care settings.

In one aspect of the disclosed telemetric dosage controller system, the computing structure encompasses a distributed architecture comprising edge devices (e.g., medication containers or wearable hubs with embedded processors, memory devices, and activatable members), communication layers (e.g., signal transmitters utilizing BTLE, Wi-Fi, or cellular protocols), and backend servers or cloud-based platforms for data aggregation and analytics. An electronic health record (EHR) system integrates seamlessly as a centralized, interoperable node within this structure, serving as a persistent repository for user-specific medical data. For instance, the telemetric dosage controller system's control logic may interface with EHR APIs, such as those conforming to HL7 FHIR standards, to transmit actuation-derived data—including timestamped medication deliveries, dosage quanta administered, and adherence metrics—directly into the patient's digital record. Conversely, the EHR can push updates to the telemetric system, such as revised drug types, adjusted scheduled delivery intervals, or new user profile parameters following a provider's consultation, enabling dynamic reconfiguration of the onboard memory and logic without manual intervention.

This integration enhances the overall computing robustness by facilitating bidirectional, secure data flows that bridge local edge processing with enterprise-level health information systems. In embodiments, the telemetric dosage controller system employs encryption protocols (e.g., AES-256) during transmission to ensure compliance with privacy regulations like HIPAA, while the EHR acts as a hub for multi-modal data fusion, incorporating telemetric inputs alongside clinical notes, lab results, and imaging. Such a setup allows for real-time synchronization; for example, low-reserve alerts from container sensors could trigger automated EHR queries to verify prescription renewals, subsequently relaying approval signals back to the system for firmware updates or refill notifications. Relatedly, the computing structure may leverage EHR-derived machine learning models deployed to edge devices, predicting actuation patterns based on historical records to preempt non-compliance.

In various embodiments, the disclosed telemetric dosage controller system for dosage control and delivery incorporates diverse powering and energy mechanisms to ensure reliable operation across its edge devices, such as medication containers, wearable hubs, or centralized organizers with activatable buttons and signal transmitters. These mechanisms are designed to accommodate the system's computational demands, including control logic execution, data transmission, and sensor operations, while prioritizing user convenience, portability, and longevity.

In one embodiment, the activatable member of the disclosed telemetric dosage controller system, such as a button or sensor-equipped switch for initiating medication tracking, can be coupled to medication containers or associated devices via an adjustable band mechanism designed to encircle cylindrical or irregularly shaped prescription bottles. For instance, the adjustable band may comprise a flexible polymer strap with a ratcheting or sliding buckle system, allowing users to customize the fit around varying container diameters, from standard pill vials to larger supplement jars. The activatable member is affixed to the band's exterior surface, positioned for ergonomic access during administration, while embedded wiring or wireless connections link it to the system's signal transmitter and memory devices housed within a compact module on the band. This implementation facilitates non-permanent attachment, enabling easy transfer between containers as prescriptions are refilled, and supports integration with tamper-evident seals to ensure secure coupling without compromising container integrity. Advantages include enhanced versatility for diverse bottle sizes, reduced risk of detachment during handling, and user-friendly installation that accommodates individuals with limited dexterity, thereby promoting consistent actuation and adherence monitoring in home or travel settings.

In another embodiment, elastic bands serve as a resilient coupling means for securing the activatable member to medication bottles or portable devices like inhalers or auto-injectors. The elastic band, fabricated from durable silicone or latex-free materials, stretches to conform to the container's contours, with the activatable member mounted on a reinforced patch along the band's length to maintain positional stability. Embodiments may incorporate multiple elastic loops for added grip or modular clips that allow the member to be detached for cleaning or replacement. This approach ensures a snug, vibration-resistant fit, particularly beneficial for ambulatory users, and can be augmented with anti-slip textures to prevent sliding on smooth glass or plastic surfaces. Related advantages encompass cost-effectiveness due to the simplicity of materials, rapid application without tools, and adaptability to irregularly shaped devices, such as oval ointment tubes, which minimizes setup barriers and enhances the system's scalability across various therapeutic modalities.

It is further contemplated that Velcro-based fastening systems provide a reusable and adjustable coupling for the activatable member, wherein hook-and-loop strips are adhered to both the member module and the medication container or device. For example, a Velcro strap wraps around a prescription bottle, with the activatable button integrated into a Velcro-compatible pad that mates securely yet allows for repositioning as needed. Variations could include magnetic-assisted Velcro for one-handed operation or embedded RFID tags within the fastening for automatic device recognition upon coupling. This method excels in scenarios requiring frequent decoupling, such as during pharmacy refills or device inspections. Advantages include strong yet reversible adhesion, suitability for textured or non-porous surfaces, and improved accessibility for users with arthritis or fine motor challenges, ultimately fostering reliable telemetric data capture by ensuring the activatable member remains proximally aligned with the medication source.

In additional embodiments, adhesive couplings offer a semi-permanent or permanent attachment option for the activatable member, utilizing pressure-sensitive adhesives, double-sided tapes, or medical-grade epoxies applied to the member's base for direct bonding to medication bottles or devices. Exemplary implementations might feature peel-and-stick pads with residue-free removal formulas, allowing affixation to the side or lid of a vial without obstructing labels or dispensing mechanisms, while waterproof variants ensure durability in moist environments like bathrooms. For enhanced security, adhesives could be combined with tamper-detection sensors that alert the control logic to unauthorized removal attempts. Advantages of this approach include minimal profile addition to maintain container aesthetics and portability, high stability against accidental dislodgement during transport, and seamless integration with disposable containers in acute care settings, thereby optimizing the telemetric dosage controller system's performance in precision tracking and remote data communication.

Network Environment

Shown in FIG. 1 is an exemplary network system 100 for executing the principles disclosed. In the illustrated implementation, the network system 100 includes an analytics server system 105, telemetric dosage controller system 110, one or more computing databases 111a and 111b, all of which can be communicatively coupled to a network 115. Also connected to the network 115 are two or more endpoint devices 125a . . . 125n and an intelligence server 138.

It is appreciated that the implementation of the analytics server system 105 and/or the intelligence server 138 may be physically structured in various configurations. In one embodiment, the one or more computing device processors that execute the functions of the analytics server system 105 and/or the intelligence server 138 may be co-located at a single geographical location or housed within a single data center. Alternatively, the one or more computing device processors that execute the functions of the analytics server system 105 and/or the intelligence server 138 may be realized in a distributed computing environment, where multiple computing device processors are spread across disparate physical locations and are communicatively coupled over a network to operate in a coordinated or parallel fashion.

According to one embodiment, the analytics server system 105 includes a computing device such as a content server (e.g., a remote server), a communication server, a laptop computer, a desktop computer, a handheld computing device, a tablet computing device, a virtual machine, a cloud-based computing system and/or a cloud-based service, and/or the like. The analytics server system 105 may include a plurality of computing devices configured to communicate with one another and/or communicate with other systems comprised in the network system 100 to implement the techniques described herein. It is appreciated that the analytics server 105 can be configured to receive and log actuation events associated with the activatable member of the disclosed the telemetric dosage controller system 110. In addition, the analytics server 105 may initiate computing operations associated with the disclosed the telemetric dosage controller system 110 such as transmitting firmware update information to the telemetric dosage controller system 110, generating reports associated with the telemetric dosage controller system 110, initiating prescription refills associated with the telemetric dosage controller system 110, etc.

According to one embodiment, the analytics server system 105 comprises a data unit 136 (also referred to as one or more data units elsewhere herein) and at least one local computing database 111a. For example, results from implementing the disclosed methods may be stored in the local computing database 111a or in a remote computing database 111b that is physically distal (e.g., implemented in a first location that is different from a second location where the local computing database 111a is implemented). According to one embodiment, the local computing database 111a and the remote computing database 111b may include a non-volatile memory or similar permanent storage device and media. For example, the local computing database 111a and the remote computing database 111b can be a hard disk drive, a CD-ROM device, a DVD-ROM device, a DVD-RAM device, a DVD-RW device, a flash memory device, solid state media, or some other mass storage device known in the art for storing information on a more permanent basis.

Figure 2:
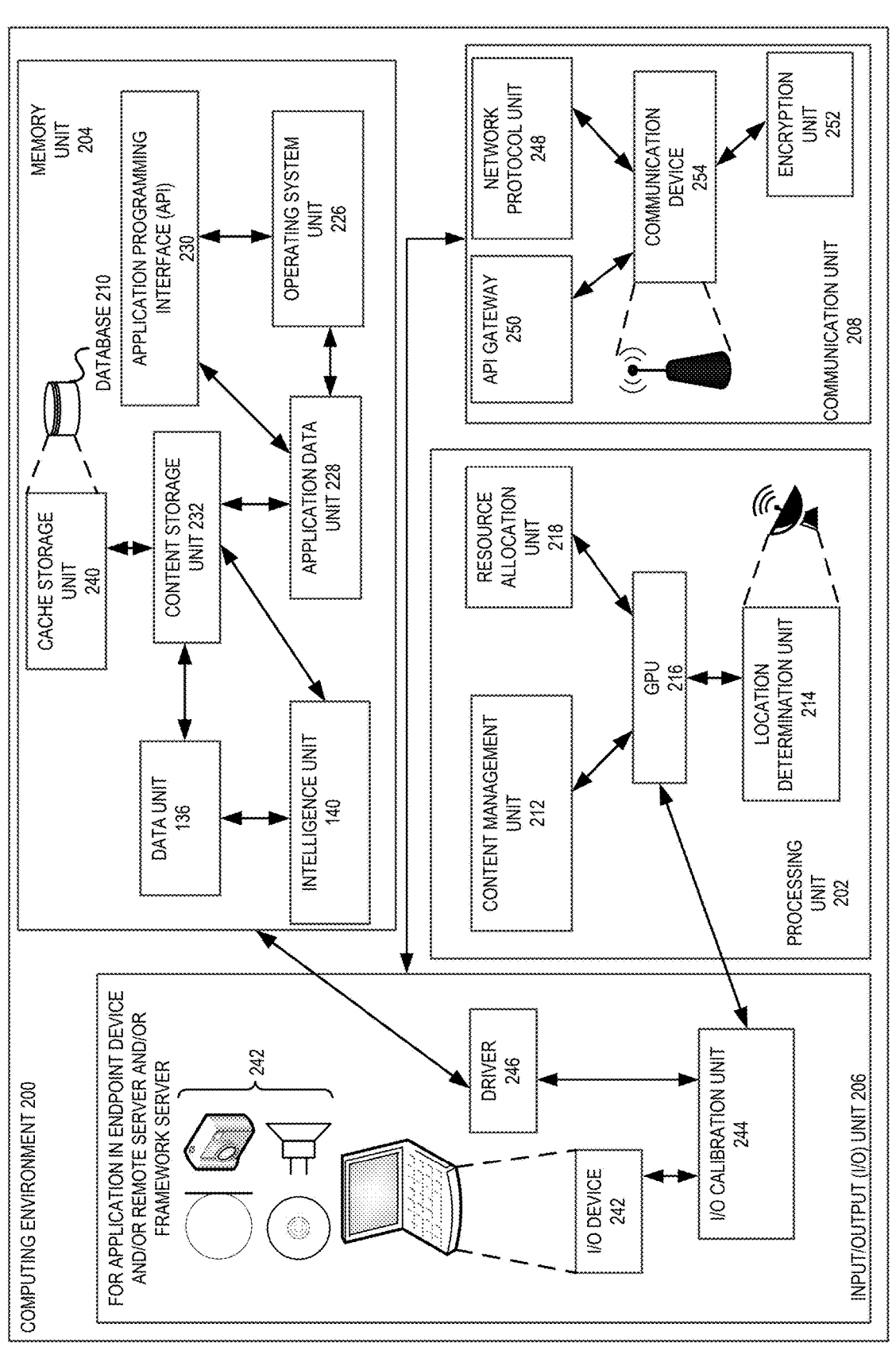
FIGS. 2 and 3 illustrate exemplary system and functional diagrams of a computing environment, within which one or more systems shown in FIG. 1 can be implemented.
Figure 3:
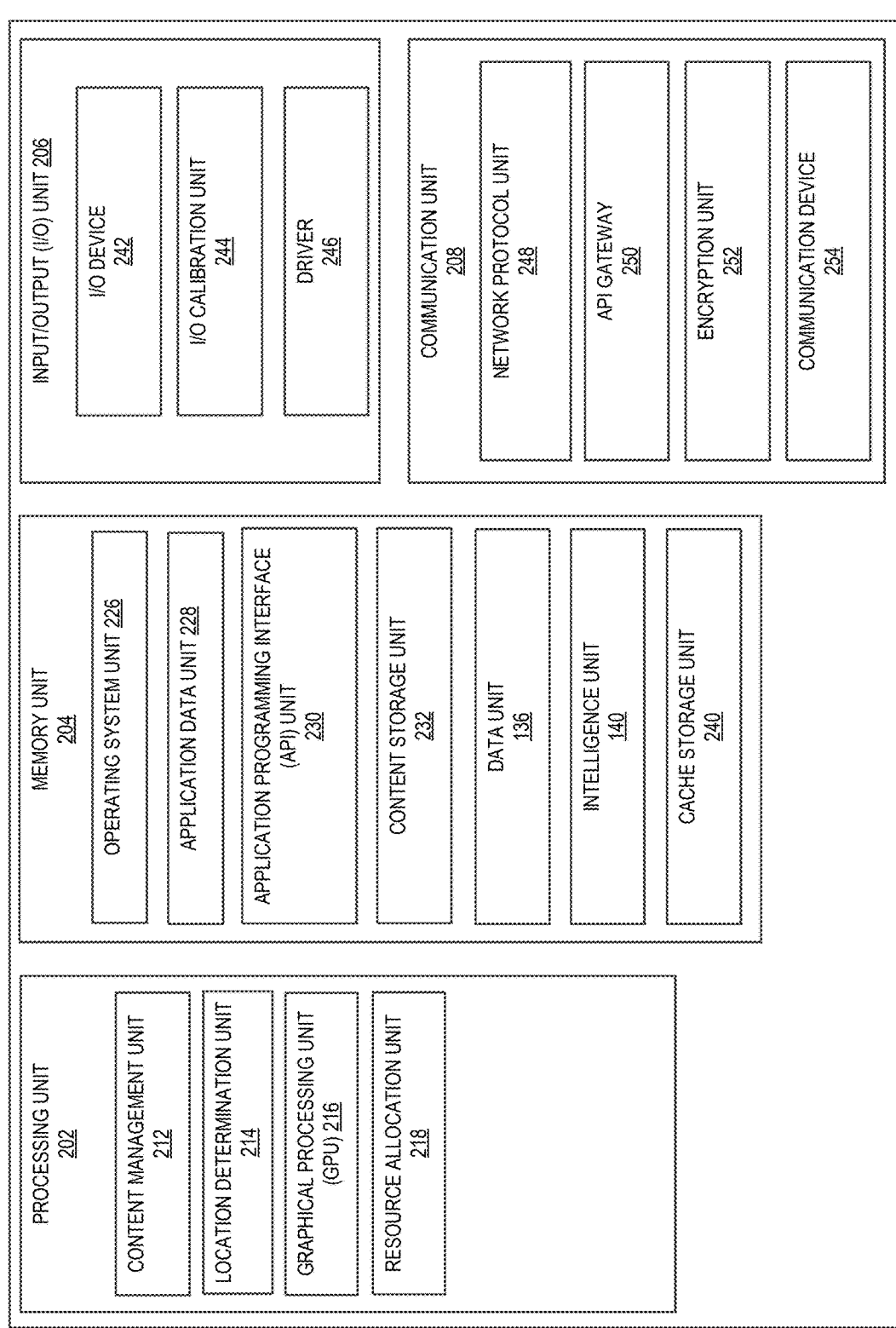

The data unit 136 referenced above may include one or more instructions or computer logic that are executed by the one or more processors such as the processors discussed in association with FIGS. 2 and 3. In addition, the data unit 136 may be independently implemented on the analytics server 105 and the telemetric dosage controller system 110 or be dependently implemented on the analytics server 105 and the telemetric dosage controller system 110 such that the dependently implemented data unit 136 may enable collaborative computing operations on the analytics server 105 and the telemetric dosage controller system 110.

In some embodiments, the data unit 136 referenced herein comprises an executable software module containing one or more instructions or computer-executable logic. These instructions are specifically configured to be executed by one or more processors, such as the processors discussed in association with FIGS. 2 and 3, to perform the disclosed steps. In particular, upon execution by said processors, the instructions within the data unit 136 causes a computing system to carry out the specific processing procedures, methods, techniques, and workflows provided in this disclosure. Thus, the data unit 136 represents a tangible software implementation that directs a computing device to function as a specialized machine for executing the disclosed method.

It is appreciated that the two or more endpoint devices 125a . . . 125n can comprise handheld computing devices, smart phones, tablets, phablets, laptop computers, desktop computers, personal digital assistants (PDAs), smart devices, wearable electronic devices, biometric devices, computer servers, virtual servers, virtual machines, and/or communication servers. In some embodiments, the two or more endpoint devices 125a, . . . , 125n may include a plurality of computing devices configured to communicate with one another and/or receive/transmit data (e.g., reports) communications from/to the analytics server system 105 and/or the intelligence server 138. It is appreciated that one or more data communications associated with executing one or more of the disclosed methods may be visualized on one or more display devices of the two or more endpoint devices 125a, . . . , 125n. In some cases, the two or more endpoint devices 125a, . . . , 125n comprise a first endpoint device that is associated with the analytics server system 105. This first endpoint device, for example, can comprise an admin endpoint device configured to monitor, control, or otherwise regulate or validate various computing operations implemented in the network system 100. Furthermore, the two or more endpoint devices 125a, . . . , 125n can include a second endpoint device that may be dependent or independent from the analytics server system 105. This second endpoint point device, for example, may be associated with displaying a data communication from the telemetric dosage controller system 110. In addition, the one or more endpoint devices 125a, . . . , 125n may include a third endpoint device that is dependent or independent of the analytics server system 105. This third endpoint device may be associated with stakeholders (e.g., medical practitioners) associated one or more data profiles comprised in the computing databases 111a or 111b.

According to one embodiment, the analytics server system 105 can be coupled, via the network 115, to the intelligence server 138 configured to control or regulate, in conjunction with, or independent of the data unit 136, training and/or using one or more computing models configured for implementing intelligence computing operations. In some cases, the intelligence server 138 can comprise one or more intelligence units 140 that can implement computing operations such as: zero-shot learning computing operations; few-shot learning computing operations; and result/model fine-tuning computing operations. Additionally or alternatively, one or more intelligent artificial intelligence (AI) models and/or machine learning (ML) models may comprise, or be based on at least one of: GPT-4, LLaMA-3, BLOOM, PaLM, GPT-3.5, BERT, Gemini, LaMDA, Perplexity, or Falcon. Additionally or alternatively, one or more of the AI or ML models may also include multiple intelligence models and therefore may be configured to perform and/or execute multiple processes in parallel. In addition, the AI or ML models disclosed may include various artificial intelligence systems or structures, including but not limited to large language models (LLMs), deep learning models, machine learning models, neural networks (e.g., convolutional neural networks (CNNs), recurrent neural networks (RNNs), transformers), expert systems, decision trees, and reinforcement learning models.

Additionally or alternatively, one or more of the AI/ML models may also include multiple intelligence models (e.g., separately trained intelligence models) and therefore may be configured to perform and/or execute multiple processes in parallel. In some embodiments, the intelligence server 138 may include a special chipset for processing large amounts of data and/or complex computing operations in a reduced amount of time. These chipsets may include, but are not limited to, Graphics Processing Units (GPUs), Tensor Processing Units (TPUs), Field-Programmable Gate Arrays (FPGAs), Application-Specific Integrated Circuits (ASICs) specifically designed for artificial intelligence (AI) workloads, or neuromorphic chips. Such chipsets can be configured to have parallel computing architectures, enabling efficient execution of matrix multiplications and convolutions, which comprise computing operations in a given intelligence model, particularly deep learning models. This parallel processing capability can allow for rapid ingestion, analysis, and processing of vast datasets, thereby accelerating model training, inference, and overall performance of the intelligence server 138 and/or analytics server system 105. The chipsets referenced herein may further incorporate dedicated memory architectures (e.g., High Bandwidth Memory (HBM)) optimized for the data throughput requirements of large intelligence models.

In some embodiments, the intelligence model(s) 140, or components thereof, may be implemented and/or deployed on dedicated hardware accelerators embedded within a system-on-chip (SoC) or as discrete integrated circuits. These hardware implementations can facilitate high-speed data processing and low-latency inference, needed for real-time applications. Furthermore, the intelligence server 138, or components thereof, including specialized chipsets and intelligence models, may be provided by a third-party vendor or service provider (e.g., via cloud-based AI/ML platforms) or may be developed and maintained in-house.

System Environment

FIGS. 2 and 3 illustrate exemplary system and functional diagrams of a computing environment 200, within which one or more systems shown in FIG. 1 can be implemented. Specifically, FIG. 2 provides a system diagram of the computing environment, whereas FIG. 3 provides a detailed functional diagram of the computing environment 200.

The computing environment 200 may include a processing unit 202, a memory unit 204, an I/O unit 206, and a communication unit 208. The processing unit 202, the memory unit 204, the I/O unit 206, and the communication unit 208 may include one or more subunits for performing operations described in this disclosure. Additionally, each unit and/or subunit may be operatively and/or otherwise communicatively coupled with each other and to the network 115 of FIG. 1. The computing environment 200 may be implemented on general-purpose hardware and/or specifically-purposed hardware as the case may require.

The processing unit 202 may control one or more of the memory unit(s) 204, the I/O unit 206, and the communication unit 208 of the computing environment 200, as well as any included subunits, elements, components, devices, and/or functions performed by the memory unit 204, I/O unit 206, and the communication unit 208. The described subelements of the computing environment 200 may also be included in similar fashion in any of the other units and/or devices included in the network system 100 of FIG. 1. Additionally, any actions described as being performed by a processor may be executed by the processing unit 202 of FIG. 2 alone and/or by the processing unit 202 in conjunction with one or more additional processors, units, subunits, elements, components, devices, and/or the like.

Further, while one processing unit 202 may be shown in FIG. 2, multiple processing units may be present and/or otherwise included in the computing environment 200 or elsewhere in the network system 100 of FIG. 1. Thus, while instructions may be described as being executed by the processing unit 202 (and/or various subunits of the processing unit 202), the instructions may be executed simultaneously, serially, and/or otherwise by one or multiple processing units 202 on one or more computing devices.

In some embodiments, the processing unit 202 may be implemented as one or more computer processing unit (CPU) chips and/or graphical processing unit (GPU) chips and may include a hardware device capable of executing computer instructions. The processing unit 202 may execute instructions, codes, computer programs, and/or scripts. The instructions, codes, computer programs, and/or scripts may be received from and/or stored in the memory unit 204, the I/O unit 206, the communication unit 208, subunits, and/or elements of the aforementioned units, other devices, and/or computing environments, and/or the like.

In some embodiments, the processing unit 202 may include, among other elements, subunits such as a content management unit 212, a location determination unit 214, a graphical processing unit (GPU) 216, and a resource allocation unit 218. Each of the aforementioned subunits of the processing unit 202 may be communicatively and/or otherwise operably coupled with each other.

The content management unit 212 may facilitate generation, modification, analysis, transmission, and/or presentation of content. Content may be file content, media content, image content, video content, textual content, audio-visual content, or any combination thereof. In some instances, content on which the content management unit 212 may operate includes device information, user interface data, images, text, themes, audio files, video files, documents, and/or the like. Additionally, the content management unit 212 may control (e.g., format) the audio-visual environment and/or appearance of application data during execution of various processes. In some embodiments, the content management unit 212 may interface with a third-party content server and/or memory location for execution of its operations.

The location determination unit 214 may facilitate detection, generation, modification, analysis, transmission, and/or presentation of location information. Location information may include global positioning system (GPS) coordinates, an Internet protocol (IP) address, a media access control (MAC) address, geolocation information, a port number, a server number, a proxy name and/or number, device information (e.g., a serial number), an address, a zip code, and/or the like. In some embodiments, the location determination unit 214 may include various sensors, radar, and/or other specifically-purposed hardware elements for the location determination unit 214 to acquire, measure, and/or otherwise transform location information.

The GPU 216 may facilitate generation, modification, analysis, processing, transmission, and/or presentation of content described above. In some embodiments, the GPU 216 may be used to render content for presentation on a computing device via, for example, a graphical display device or a graphical user interface (GUI) of a display device of the endpoint device 125*a*. The GPU 216 may also include multiple GPUs and therefore may be configured to perform and/or execute multiple processes in parallel.

The resource allocation unit 218 may facilitate the determination, monitoring, analysis, and/or allocation of computing resources throughout the computing environment 200 and/or other computing environments. For example, the computing environment may facilitate a high volume of data to be processed and analyzed. As such, computing resources of the computing environment 200 used by the processing unit 202, the memory unit 204, the I/O unit 206, and/or the communication unit 208 (and/or any subunit of the aforementioned units) such as processing power, data storage space, network bandwidth, and/or the like may be in high demand at various times during operation. Accordingly, the resource allocation unit 218 may include sensors and/or other specially-purposed hardware for monitoring performance of each unit and/or subunit of the computing environment 200, as well as hardware for responding to the computing resource needs of each unit and/or subunit. In some embodiments, the resource allocation unit 218 may use computing resources of a second computing environment separate and distinct from the computing environment 200 to facilitate a desired operation. For example, the resource allocation unit 218 may determine a number of simultaneous computing processes and/or requests. The resource allocation unit 218 may also determine that the number of simultaneous computing processes and/or requests meet and/or exceed a predetermined threshold value. Based on this determination, the resource allocation unit 218 may determine an amount of additional computing resources (e.g., processing power, storage space of a particular non-transitory computer-readable memory medium, network bandwidth, and/or the like) required by the processing unit 202, the memory unit 204, the I/O unit 206, the communication unit 208, and/or any subunit of the aforementioned units for safe and efficient operation of the computing environment while supporting the number of simultaneous computing processes and/or requests. The resource allocation unit 218 may then retrieve, transmit, control, allocate, and/or otherwise distribute determined amount(s) of computing resources to each element (e.g., unit and/or subunit) of the computing environment 200 and/or another computing environment.

The memory unit 204 may be used for storing, recalling, receiving, transmitting, and/or accessing various files and/or data during operations within the computing environment 200. In one embodiment, the memory unit 204 stores instructions, code, and/or data that may be executed by the processing unit 202. For instance, the memory unit 204 may store code that execute operations associated with one or more units and/or one or more subunits of the computing environment 200. For example, the memory unit may store code for the processing unit 202, the I/O unit 206, the communication unit 208, and for itself. Moreover, the memory unit may store code for implementing the data unit 136 associated with the analytics server system 105. Furthermore, the memory unit 204 can also be used to store one or more computing models, relationship record(s) associated with category data determined during, for example, classification computing operations associated with the dosage controller system. The category data, for example, can be linked to, or characterize features of objects imaged using the dosage controller system.

Turning back to FIGS. 2 and 3, the memory unit 204 may include various types of data storage media such as solid-state storage media, hard disk storage media, virtual storage media, and/or the like. Memory unit 204 may include dedicated hardware elements such as hard drives and/or servers, as well as software elements such as cloud-based storage drives. In some implementations, memory unit 204 may include a random-access memory (RAM) device, a dynamic random-access memory (DRAM) device, a static random-access memory (SRAM) device, flash memory, read only memory (ROM) device, and/or various forms of secondary storage. The RAM device may be used to store volatile data and/or to store instructions that may be executed by the processing unit 202. For example, the instructions stored by the RAM device may be a command, a current operating state of computing environment 200, an intended operating state of computing environment 200, and/or the like. As a further example, data stored in the RAM device of memory unit 204 may include instructions related to various methods and/or functionalities described in this disclosure. The ROM device may be a non-volatile memory device that may have a smaller memory capacity than the memory capacity of a secondary storage. The ROM device may be used to store instructions and/or data that may be read during execution of computer instructions. In some embodiments, access to both the RAM device and ROM device may be faster to access than the secondary storage.

Secondary storage may comprise one or more disk drives and/or tape drives and may be used for non-volatile storage of data or as an over-flow data storage device if the RAM device is not large enough to hold all working data. Secondary storage may be used to store programs that may be loaded into the RAM device when such programs are selected for execution. In some embodiments, the memory unit 204 includes one or more databases 210 for storing any data described herein. For example, depending on the implementation, the one or more databases 210 may be used as the local computing database 111*a* or remote computing database 111*b* associated with the analytics server system 105. In some embodiments, the memory unit 204 and/or its subunits may be local relative to the analytics server system 105 and/or be remotely located relative to the analytics server system 105.

The memory unit 204 may include subunits such as an operating system unit 226, an application data unit 228, an application programming interface (API) unit 230, a content storage unit 232, and a cache storage unit 240. Each of the aforementioned subunits of the memory unit 204 may be communicatively and/or otherwise operably coupled with each other and other units and/or subunits of the computing environment 200. It is also noted that the memory unit 204 may include other modules, instructions, or code that facilitate the execution of the techniques described. For instance, the memory unit 204 may include the data unit 136 and the intelligence unit 140. The data unit 136 and/or intelligence unit 140 may be configured to implement one or more of the computing methods or operations. According to one embodiment, the data unit 136 and/or the intelligence unit 140 comprise one or more of a analytic data flux processor (ADFP), a cognitive data orchestration unit (CDOU), an insight generation hypervisor (IGH), a metric derivation computational fabric (MDCF), a phenomenological data synthesizer (PDS), a quantitative intelligence abstraction engine (QIAE), an adaptive data analytics core (ADAC), a contextual insight graph engine (CIGE), an empirical data transformation array (EDTA), or a heuristic data pattern extractor (HDPE).

The operating system unit 226 may facilitate deployment, storage, access, execution, and/or utilization of an operating system used by computing environment 200 and/or any other computing environment described in this disclosure. In some embodiments, operating system unit 226 may include various hardware and/or software elements that serve as a structural platform for the processing unit 202 to execute various operations described herein. Operating system unit 226 may further store various pieces of information and/or data associated with the operation of the operating system and/or computing environment 200 as a whole, such as a status of computing resources (e.g., processing power, memory availability, resource utilization, and/or the like), runtime information, modules to direct execution of operations described herein, user permissions, security credentials, and/or the like.

The application data unit 228 may facilitate deployment, storage, access, execution, and/or utilization of an application used by computing environment 200 and/or any other computing environment described herein. For example, an endpoint device (e.g., endpoint device 125*a*) may be required to download, install, access, and/or otherwise use a software application (e.g., web application) to facilitate performance of one or more of the disclosed computing operations. As such, application data unit 228 may store any information and/or data associated with an application. Application data unit 228 may further store various pieces of information and/or data associated with the operation of an application and/or computing environment 200 as a whole, such as a status of computing resources (e.g., processing power, memory availability, resource utilization, and/or the like), runtime information, user interfaces, modules to direct execution of operations described herein, user permissions, security credentials, and/or the like.

The API unit 230 may facilitate deployment, storage, access, execution, and/or use of information associated with APIs of computing environment 200 and/or any other computing environment described in this disclosure. For example, computing environment 200 may include one or more APIs for various devices, applications, units, subunits, elements, and/or other computing environments to communicate with each other and/or use the same data. Accordingly, API unit 230 may include API databases containing information that may be accessed and/or used by applications, units, subunits, elements, and/or operating systems of other devices and/or computing environments. In some embodiments, each API database may be associated with a customized physical circuit included in memory unit 204 and/or API unit 230. Additionally, each API database may be public and/or private, and so authentication credentials may be required to access information in an API database. In some embodiments, the API unit 230 may enable the analytics server system 105 and/or the display device of the endpoint device 125*a* to communicate with each other.

The content storage unit 232 may facilitate deployment, storage, access, and/or utilization of information associated with performance of the disclosed operations by computing environment 200 and/or any other computing environment described. In some embodiments, content storage unit 232 may communicate with content management unit 212 to receive and/or transmit content files (e.g., media content, image data, video data, audio-visual data, visualization data, etc.).

The cache storage unit 240 may facilitate short-term deployment, storage, access, analysis, and/or use of data. In some embodiments, cache storage unit 240 may serve as a short-term storage location for data so that the data stored in cache storage unit 240 may be accessed quickly. In some instances, cache storage unit 240 may include RAM devices and/or other storage media types for quick recall of stored data. Cache storage unit 240 may include a partitioned portion of storage media included in memory unit 204.

The I/O unit 206 may include hardware and/or software elements for the computing environment 200 to receive, transmit, and/or present information useful for performing processes described herein. For example, elements of the I/O unit 206 may be used to receive input from the analytics server system 105. As described, I/O unit 206 may include subunits such as an I/O device 242, an I/O calibration unit 244, and/or driver 246.

The I/O device 242 may facilitate receipt, transmission, processing, presentation, display, input, and/or output of information as a result of executed processes described in this disclosure. In some embodiments, the I/O device 242 may include a plurality of I/O devices. In some embodiments, device 242 may include a variety of elements that enable a user to interface with computing environment 200. For example, I/O device 242 may include a keyboard, a touchscreen, a button, a sensor, a biometric scanner, a laser, a microphone, a dosage controller system, and/or another element for receiving and/or collecting input from a user. Additionally, and/or alternatively, I/O device 242 may include a display, a screen, a sensor, a vibration mechanism, a light emitting diode (LED), a speaker, a radio frequency identification (RFID) scanner, and/or another element for presenting and/or otherwise outputting data to a user. In some embodiments, the I/O device 242 may communicate with one or more elements of processing unit 202 and/or memory unit 204 to execute the disclosed operations.

The I/O calibration unit 244 may facilitate the calibration of the I/O device 242. For example, I/O calibration unit 244 may detect and/or determine one or more settings of I/O device 242 and then adjust and/or modify settings and/or format and/or optimize viewing of a graphical user interface and/or one or more visualizations associated with alerts or alert data communications. According to some embodiments, the I/O calibration unit 244 may be used to format or resolve, for example, data communications such as alerts into multidimensional data components (e.g., multi-modal data including multiple aspects such as image data, video data, textual data, etc.) and rendering the multidimensional data components on a display device.

In some embodiments, the I/O calibration unit 244 may use a driver 246 (or multiple drivers) to calibrate I/O device 242. For example, driver 246 may include software that is installed by I/O calibration unit 244 so that an element of computing environment 200 (or an element of another computing environment) may recognize and/or integrate with I/O device 242 for disclosed processes.

The communication unit 208 may facilitate establishment, maintenance, monitoring, and/or termination of data communications (e.g., control or alert data communications) between computing environment 200 and other computing environments, third party server systems, and/or the like. Communication unit 208 may also facilitate internal communications between various elements (e.g., units and/or subunits) of computing environment 200. In some embodiments, communication unit 208 may include a network protocol unit 248, an API gateway 250, an encryption unit 252, and/or a communication device 254. Communication unit 208 may include hardware and/or software elements.

The network protocol unit 248 may facilitate establishment, maintenance, and/or termination of a communication connection for computing environment 200 by way of a network. For example, the network protocol unit 248 may detect and/or define a communication protocol required by a particular network and/or network type. Communication protocols used by the network protocol unit 248 may include Wi-Fi protocols, Li-Fi protocols, cellular data network protocols, Bluetooth® protocols, WiMAX protocols, Ethernet protocols, powerline communication (PLC) protocols, and/or the like. In some embodiments, facilitation of communication for computing environment 200 may include transforming and/or translating data from being compatible with a first communication protocol to being compatible with a second communication protocol. In some embodiments, network protocol unit 248 may determine and/or monitor an amount of data traffic to consequently determine which particular network protocol is to be used for establishing a secure communication connection, transmitting data, and/or performing the disclosed methods and/or data visualization operations and/or other processes provided in this disclosure.

The API gateway 250 may allow other devices and/or computing environments to access API unit 230 of memory unit 204 of computing environment 200. For example, display devices associated with the various systems of FIG. 1 may access API unit 230 of computing environment 200 via API gateway 250. In some embodiments, API gateway 250 may be required to validate user credentials associated with a user of a display device prior to providing access to API unit 230 to a user. API gateway 250 may include instructions for computing environment 200 to communicate with another device and/or between elements of the computing environment 200.

The encryption unit 252 may facilitate translation, encryption, encoding, decryption, and/or decoding of information received, transmitted, and/or stored by the computing environment 200. Using encryption unit 252, each transmission of data may be encrypted, encoded, and/or translated for security reasons, and any received data may be encrypted, encoded, and/or translated prior to its processing and/or storage. In some embodiments, encryption unit 252 may generate an encryption key, an encoding key, a translation key, and/or the like, which may be transmitted along with any data content.

The communication device 254 may include a variety of hardware and/or software specifically purposed to facilitate communication for computing environment 200. In some embodiments, communication device 254 may include one or more radio transceivers, chips, analog front end (AFE) units, antennas, processing units, memory, other logic, and/or or other components to implement communication protocols (wired or wireless) and related functionality for facilitating communication for computing environment 200. Additionally and/or alternatively, communication device 254 may include a modem, a modem bank, an Ethernet device such as a router or switch, a universal serial bus (USB) interface device, a serial interface, a token ring device, a fiber distributed data interface (FDDI) device, a wireless local area network (WLAN) device and/or device component, a radio transceiver device such as code division multiple access (CDMA) device, a global system for mobile communications (GSM) radio transceiver device, a universal mobile telecommunications system (UMTS) radio transceiver device, a long term evolution (LTE) radio transceiver device, a worldwide interoperability for microwave access (WiMAX) device, and/or another device used for communication purposes.

In some embodiments, intelligence unit 140 comprises an executable software module containing one or more instructions or computer-executable logic. These instructions are specifically configured to be executed by one or more processors, such as the processors discussed in association with FIGS. 2 and 3, to perform computing operations of the intelligence server 138.

EMBODIMENTS

The disclosed telemetric dosage controller system is configured for improving medication adherence through substantially real-time dosage tracking and medication delivery management. According to one embodiment, the telemetric dosage controller system comprises: at least one activatable member configured to be actuated upon administration of a first medication thereby triggering an actuation event of the system that initiates electronic tracking of a medication administration event associated with the first medication. It is appreciated that the medication administration event represents a delivery of the first medication to a first biological system (e.g., a patient).

The telemetric dosage controller system can also include a signal transmitter operatively coupled to the at least one activatable member and which is configured to transmit or receive data signals via at least one wireless network. According to one embodiment, the signal transmitter relays one or more of: timestamp data associated with the actuation event; dosage verification data associated with the first medication; and identifier data associated with an electronic health record (EHR) of the first biological system.

The telemetric dosage controller system can also comprise one or more non-transitory memory devices storing control logic customized to the identifier data associated with the electronic health record of the first biological system. In one embodiment, customizing the control logic to identifier data associated with the EHR involves adapting the telemetric dosage controller system's control logic and operational parameters to the attributes of a specific biological system, as identified by data such as the name of the biological system, medical record information of the biological system, or other identifiers within the EHR. This customization ensures that the telemetric dosage controller system's functions—such as tracking medication administration events, correlating dosage parameters, and adjusting delivery schedules—are personalized to the specific medical profile of the biological system, including their prescribed medications, health conditions, and treatment plans. For instance, the control logic may map actuation events to the patient's drug type, dosage quanta, and delivery intervals as recorded in the EHR, while also integrating physiological feedback or patient-reported outcomes specific to that biological system. By leveraging identifier data, the telemetric dosage controller system ensures accurate, patient-specific monitoring and management, enhancing medication adherence and minimizing risks in complex scenarios like polypharmacy, while maintaining compliance with healthcare standards.

According to one embodiment, the control logic is configured to: correlate or map the actuation event with dosage parameters including: a drug type parameter associated the first medication; dosage quanta data associated with delivery of the first medication to the first biological system; and delivery interval data associated with a first temporal window between a first delivery of the first medication to the first biological system, and a second delivery of the first medication to the first biological system; and dynamically adjusting the dosage parameters based on physiological or biomarker data associated with delivery of the first medication to the first biological system, or a second medication. Dynamically adjusting the dosage parameters can also be based on response data associated with: a first detected effect of the first medication on the first biological system; a second detected effect of a second medication on the first biological system; or a third detected effect of a third medication on the first biological system or a second biological system.

The disclosed telemetric dosage controller system comprises a powering mechanism configured to supply energy to components of the telemetric dosage controller system, the powering mechanism including at least one of: a rechargeable battery system coupled to, or integrated into the telemetric dosage controller system; a disposable battery system configured to power the telemetric dosage controller system for a second temporal window; a wireless charging energy system configured to wirelessly charge or power the telemetric dosage controller system; or an energy harvesting system configured to use kinetic energy, thermoelectric energy, or vibrational energy associated with the first biological system.

It is appreciated that actuating the at least one activatable member triggers the signal transmitter of the telemetric dosage controller system to securely transmit encrypted data to a server for substantially real-time monitoring, automated alert generation, and adherence management associated with at least the first medication.

These and other implementations may each optionally include one or more of the following features.

Figures 4A, 4B, 4C:
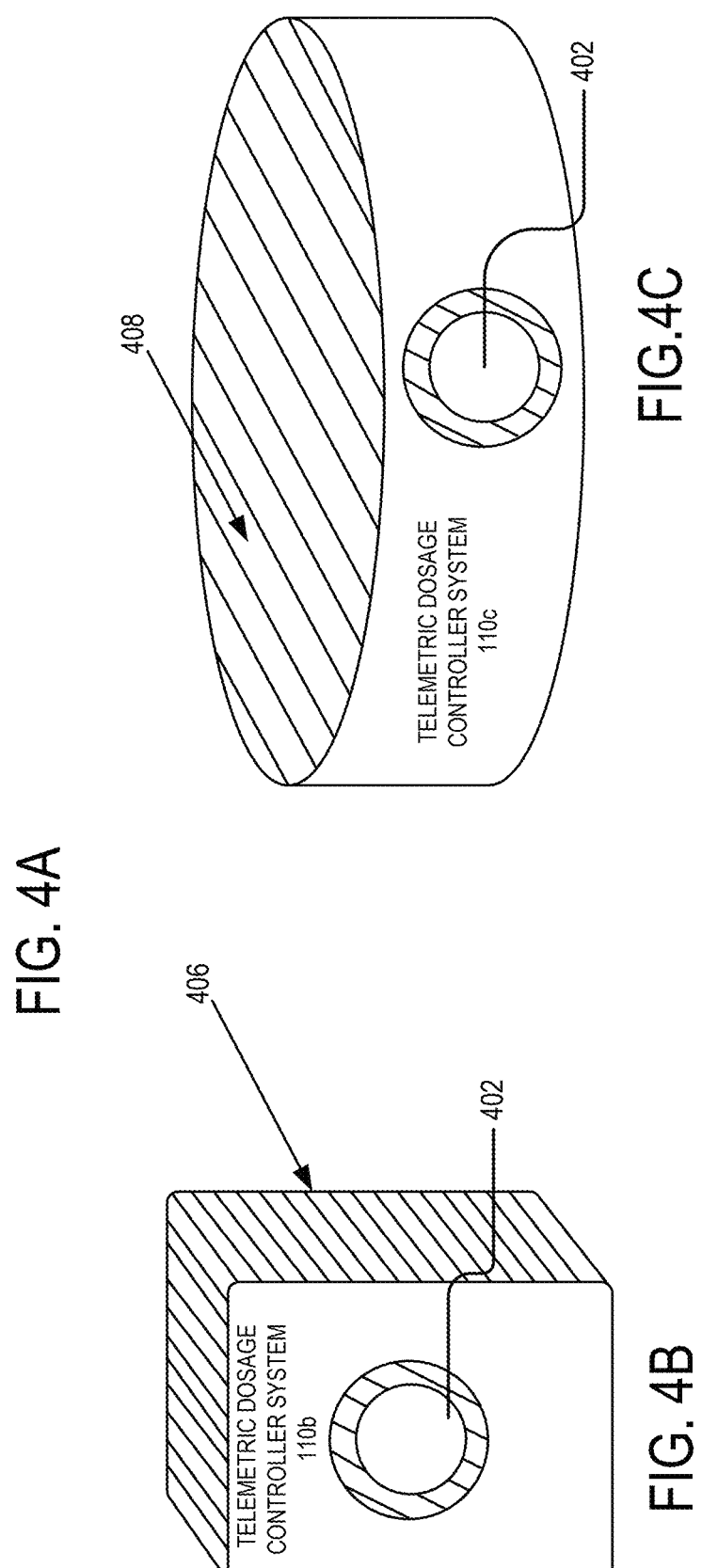
FIGS. 4A-4C show exemplary implementations of the disclosed telemetric control systems.

The at least one activatable member can comprise a button or touch-sensitive interface directly coupled to a medication container or positioned proximal thereto. This coupling can be achieved via an adjustable band configured to fit around varying container diameters including a first diameter of a container within which is the first medication. For example, FIGS. 4A-4C show exemplary implementations of the disclosed telemetric dosage controller systems, each of which have at least one activatable member 402. In FIG. 4A, an adjustable band 404 can be fitted around a container containing a medication (e.g., first medication). The adjustable band can be an elastic band according to some embodiments.

In some embodiments, the at least one activatable member is coupled to a medication container via, for example, an elastic band fabricated from silicone or latex-free materials, the elastic band being structured to: stretch and thereby conform to a container contour of a container within which is placed the first medication; and incorporate an anti-slip texture for stabilizing the elastic band around the container. In other embodiments, the at least one activatable member is coupled to a medication container via a Velcro-based fastening system comprising hook-and-loop strips, allowing reusable and repositionable attachment with or without magnetic assistance for one-handed operation of the telemetric dosage controller system. FIGS. 4B and 4C, each have surfaces 406 and 408 which can be Velcro-based.

In some cases, the activatable member of the telemetric dosage controller system is coupled via adhesive means, such as pressure-sensitive adhesives or medical-grade epoxies with residue-free removal, combined with tamper-detection sensors to alert the control logic stored in the one or more non-transitory memory devices, of unauthorized removal attempts.

Furthermore, the control logic is further configured to generate, or initiate generations of a multidimensional report including: medication adherence data associated with delivering to the first biological system, the first medication or the second medication; pharmacokinetic adherence curve data indicating an assessment or prediction of how closely a medication regimen of the first medication or the second medication is observed by the first biological system; and predictive analytics data based on historical actuation patterns of the at least the one activatable member.

According to one embodiment, the multidimensional report comprises multi-modal data including visual timelines, interactive charts, and audio summaries. The multidimensional report can comprise: a timestamp data of delivering at least the first medication to the first biological system within the first temporal window, the second temporal window, or a third temporal window; dosage quanta data associated with delivering the first medication to the first biological system during the first temporal window, the second temporal window, or the third temporal window; and deviation data associated with inconsistent delivery of the first medication to the first biological system over the first temporal window, the second temporal window, or the third temporal window. It is appreciated that dosage quanta as used herein refers to the discrete, measurable units or amounts of a medication administered at a given time. In the context of your telemetric dosage controller system claim, it represents the specific quantity of the first medication delivered during a medication administration event. For example, this could be a single pill, a specific volume of liquid (e.g., 5 mL), or a defined dose of an injectable (e.g., 100 mg). The term "quanta" emphasizes the precise, individualized measurement of the dose, which the telemetric dosage controller system tracks to ensure accurate monitoring and management of medication adherence.

In some cases, the multidimensional report referenced above is configured or structured to be visualized on a display computing device in one of a Portable Document Format (PDF) file format, a Comma-Separated Values (CSV) file format, a data format associated with textual data, video data, or audiovisual data.

According to one embodiment, the telemetric dosage controller system further comprises an interface for bidirectional integration with an EHR system that is compliant with a Health Level Seven International (HL7) Fast Healthcare Interoperability Resources (FHIR) standards. Furthermore, the multidimensional report can comprise: cumulative adherence rate data indicating delivering at least the first medication to the first biological system; anomaly detection data indicating unexpected dosage variations associated with delivering at least the first medication to the first biological system; and machine learning-based risk prediction data associated with optimizing delivery of at least the first medication to the first biological system.

In some embodiments, the multidimensional report includes a substantially real-time inventory depletion forecast generated, based on actuating the at least one activatable member. The inventory depletion forecast can indicate one or more of: a time for replenishing the first medication; and a quantity of the first medication to be replenished.

According to one embodiment, the telemetric dosage controller system further comprises one or more sensor arrays interfaced with the signal transmitter for acquiring physiological data of the first biological system such as biomarker levels or vital signs of the first biological system, enabling a closed-loop feedback mechanism that informs the control logic to dynamically adjust dosage quanta or delivery intervals of delivering the first medication to the first biological system.

In some instances, the telemetric dosage controller system is configured to facilitate remote prescription submission by automatically triggering refill requests to a linked pharmacy or an EHR system based on activating the at least one activatable member.

Moreover, the signal transmitter referenced in conjunction with the disclosed telemetric dosage controller system supports over-the-air (OTA) firmware updates to the one or more non-transitory memory devices of the telemetric dosage controller system and transmission of user-specific feedback, including aggregated actuation logs and adherence metrics, to healthcare providers for adjusting the medication regimen of the first medication relative to the first biological system.

In some cases, the telemetric dosage controller system comprises: a first activatable member of the at least one activatable member which is activatable to track the first medication; a second activatable member of the at least one activatable member which is activatable to track the second medication; and a third activatable member of the at least one activatable member which is activatable to track a third medication. In such instances, first activatable member, the second activatable member, and the third activatable member can be color-coded, labeled with drug-specific indicia, or embedded with haptic patterns for tactile differentiation, and arranged in a modular container assembly or centralized hub device for independent tracking.

In some embodiments, the powering mechanism discussed above in association with the telemetric dosage controller system comprises a rechargeable lithium-ion battery with USB charging via a USB-A or micro-USB port, including a power management module that regulates charging cycles and optimize energy distribution for low-power operations between actuations of the at least one activatable member.

Furthermore, the powering mechanism can comprise a USB-C port supporting Power Delivery (PD) standards for faster charging and simultaneous data transfer during firmware updates or EHR synchronization.

In addition, the disposable battery system of the powering mechanism can comprise one of a coin-cell or alkaline battery, coin cel or alkaline battery, each of which can be housed in an accessible compartment of the telemetric dosage controller system and optimized for ultra-low power consumption through power saving modes that deactivate non-essential components from drawing energy from the powering mechanism during non-medication delivery times associated with the first medication.

In some embodiments the wireless charging energy system of the powering mechanism associated with the telemetric dosage controller system comprises wireless charging via a Qi-standard inductive charging with an embedded coil, allowing cable-free energy transfer to the telemetric dosage controller system and supporting sealed, water-resistant designs of the telemetric dosage controller system for enhanced durability in clinical or non critical environments.

According to one embodiment, the energy harvesting system referenced herein is configured to generate energy for the telemetric dosage controller system based on one or more: a piezoelectric generator embedded in the at least one activatable member, such that the piezoelectric generator converts mechanical energy from actuations of the at least one activatable member into electrical energy that powers the telemetric dosage controller system; or a photovoltaic cell for capturing and converting ambient light into electrical energy that powers the telemetric dosage controller system.

In one embodiment, the powering mechanism comprises a hybrid system with a primary rechargeable battery and a secondary disposable battery for failover, the control logic being configured to monitor battery levels and switching energy sources to maintain uninterrupted operation of the telemetric dosage controller system during power disruptions.

In some embodiments, the disclosed telemetric dosage controller system is configured for interoperability with Internet of Things (IoT) ecosystems, such that the signal transmitter communicates with external devices to contextualize dosage decisions based on environmental data, and blockchain technology for immutable logging of actuation events to ensure tamper-proof audit trails.

According to one embodiment, the at least one wireless network associated with the at least one wireless network is selected from the group consisting a Bluetooth Low Energy (BTLE) network, a Wi-Fi network, a satellite communications network, or a cellular network.

Furthermore, the terms substantially real-time and near real-time, as used herein, refer to a processing and response timeframe that is close to, but not necessarily equal to, instantaneous or true real-time. While true real-time implies a delay of zero, any practical digital system will have some inherent latency due to data processing, computation, and network transmission. Therefore, these terms describe a timeframe where this inherent latency is sufficiently short as to be negligible for the effective operation of a given process or for the perception of a human user. The specific duration considered to be substantially real-time or near real-time is application-dependent and is defined by the requirements of the system to function as intended without being materially compromised by the delay.

It is appreciated that the term optimize/optimal and its variants (e.g., efficient or optimally) may simply indicate improving, rather than the ultimate form of 'perfection' or the like.

The terminology used in this disclosure is for the purpose of describing particular exemplary embodiments and is not intended to be limiting. For example, as used herein, the singular forms "a", "an" and "the" may be intended to include plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, processes, elements, components, and/or groups thereof. The described method steps, processes, and operations are not to be construed as necessarily requiring their performance in the particular order discussed or illustrated, unless specifically identified as an order of performance. It is further appreciated that additional or alternative steps may be employed according to some implementations.

Although the terms first, second, third, etc., may be used to describe various elements, components, regions, layers and/or sections, these elements, components, regions, layers and/or sections should not be limited by these terms. These terms may be used to distinguish one element, component, region, layer or section from another element, component, region, layer or section. That is, terms such as "first," "second," and other numerical terms, when used in this disclosure, do not imply a sequence or order unless clearly indicated by the context. In addition, the term optimal and its variants (e.g., efficient, optimally, etc.) as used in this disclosure may simply indicate improving, rather than the ultimate form of 'perfection' or the like.

Reference in the specification to "one implementation" or "an implementation" means that a particular feature, structure, or characteristic described in connection with the implementation is included in at least one implementation of the disclosure. The appearances of the phrase "in one implementation," "in some implementations," "in one instance," "in some instances," "in one case," "in some cases," "in one embodiment," or "in some embodiments" in various places in the specification are not necessarily all referring to the same implementation or embodiment.

Finally, the above descriptions of the implementations of the present disclosure have been presented for the purposes of illustration and description. It is not intended to be exhaustive or to limit the present disclosure to the precise form disclosed. Many modifications and variations are possible in light of the above teaching. It is appreciated that the scope of the present disclosure be limited not by this detailed description, but rather by the claims of this application. The present disclosure may be embodied in other specific forms without departing from the spirit or essential characteristics thereof. Accordingly, the above discussed subject-matter is illustrative, but not limiting, of the scope of the present disclosure, which is set forth in the following claims.

The invention claimed is:

1. A telemetric control system for improving medication adherence through substantially real-time dosage tracking and medication delivery management, the telemetric control system comprising:

at least one activatable member configured to be actuated upon administration of a first medication thereby triggering an actuation event of the telemetric control system that initiates electronic tracking of a medication administration event associated with the first medication, the medication administration event representing a delivery of the first medication to a first biological system;

a signal transmitter operatively coupled to the at least one activatable member and configured to transmit or receive data signals via at least one wireless network, wherein the signal transmitter relays one or more of:
timestamp data associated with the actuation event,
dosage verification data associated with the first medication, and
identifier data associated with an electronic health record (EHR) of the first biological system;

one or more non-transitory memory devices storing control logic customized to the identifier data associated with the EHR of the first biological system, the control logic being configured to implement one or more of:

correlating or mapping the actuation event with dosage parameters including:
a drug type parameter associated with the first medication,
dosage quanta data associated with delivery of the first medication to the first biological system, and
delivery interval data associated with a first temporal window between a first delivery of the first medication to the first biological system, and a second delivery of the first medication to the first biological system, and dynamically adjusting the dosage parameters based on one or more of:
physiological or biomarker data associated with delivery of:
the first medication to the first biological system, or
a second medication;
response data associated with:
a first detected effect of the first medication on the first biological system,
a second detected effect of a second medication on the first biological system, or
a third detected effect of a third medication on the first biological system or a second biological system;

a powering mechanism configured to supply energy to components of the telemetric control system, the powering mechanism including at least one of:
a rechargeable battery system coupled to, or integrated into the telemetric control system,
a disposable battery system configured to power the telemetric control system for a second temporal window,
a wireless charging energy system configured to wirelessly charge or power the telemetric control system, or an energy harvesting system configured to use kinetic energy, thermoelectric energy, or vibrational energy associated with the first biological system; and wherein actuating the at least one activatable member triggers the signal transmitter to securely transmit encrypted data to a server for substantially real-time monitoring, automated alert generation, and adherence management associated with at least the first medication.

2. The telemetric control system of claim 1, wherein the at least one activatable member comprises a button or touch-sensitive interface directly coupled to a medication container or positioned proximal thereto, the coupling achieved via an adjustable band configured to fit around varying container diameters including a first diameter of a container within which is the first medication.

3. The telemetric control system of claim 2, wherein the at least one activatable member is coupled to the medication container via:

an elastic band fabricated from silicone or latex-free materials, the elastic band being structured to:

stretch and thereby conform to a container contour of a container within which is placed the first medication, and incorporate an anti-slip texture for stabilizing the elastic band around the container, or a Velcro-based fastening system comprising hook-and-loop strips, allowing reusable and repositionable attachment with or without magnetic assistance for one-handed operation of the telemetric control system.

4. The telemetric control system of claim 2, wherein the at least one activatable member is coupled via adhesive means, such as pressure-sensitive adhesives or medical-grade epoxies with residue-free removal, combined with tamper-detection sensors to alert the control logic stored in the one or more non-transitory memory devices, of unauthorized removal attempts.

5. The telemetric control system of claim 1, wherein the control logic is further configured to generate, or initiate generation of a multidimensional report including:

medication adherence data associated with delivering to the first biological system, the first medication or the second medication, pharmacokinetic adherence curve data indicating an assessment or prediction of how closely a medication regimen of the first medication or the second medication is observed by the first biological system, and predictive analytics data based on historical actuation patterns of the at least the one activatable member.

6. The telemetric control system of claim 5, wherein:

the multidimensional report comprises multi-modal data including visual timelines, interactive charts, and audio summaries, the multidimensional report comprises:

timestamp data of delivering at least the first medication to the first biological system within the first temporal window, the second temporal window, or a third temporal window, dosage quanta data associated with delivering the first medication to the first biological system during the first temporal window, the second temporal window, or the third temporal window, and deviation data associated with inconsistent delivery of the first medication to the first biological system over the first temporal window, the second temporal window, or the third temporal window, and the multidimensional report being configured to be visualized on a display computing device in one of a Portable Document Format (PDF) file format, a Comma-Separated Values (CSV) file format, a data format associated with textual data or video data or audiovisual data.

7. The telemetric control system of claim 5, wherein:

the telemetric control system further comprises an interface for bidirectional integration with an EHR system that is compliant with a Health Level Seven International (HL7) Fast Healthcare Interoperability Resources (FHIR) standards, the multidimensional report comprises:

cumulative adherence rate data indicating delivering at least the first medication to the first biological system, anomaly detection data indicating unexpected dosage variations associated with delivering at least the first medication to the first biological system, and machine learning-based risk prediction data associated with optimizing delivery of at least the first medication to the first biological system.

8. The telemetric control system of claim 5, wherein the multidimensional report includes a substantially real-time inventory depletion forecast generated, based on actuating the at least one activatable member, the inventory depletion forecast indicating one or more of:

a time for replenishing the first medication, and a quantity of the first medication to be replenished.

9. The telemetric control system of claim 1, further comprising one or more sensor arrays interfaced with the signal transmitter for acquiring physiological data of the first biological system such as biomarker levels or vital signs of the first biological system, enabling a closed-loop feedback mechanism that informs the control logic to dynamically adjust dosage quanta or delivery intervals of delivering the first medication to the first biological system.

10. The telemetric control system of claim 1, wherein the telemetric control system is configured to facilitate remote prescription submission by automatically triggering refill requests to a linked pharmacy or an EHR system based on activating the at least one activatable member.

11. The telemetric control system of claim 1, wherein the signal transmitter supports over-the-air (OTA) firmware updates to the one or more non-transitory memory devices of the telemetric control system and transmission of user-specific feedback, including aggregated actuation logs and adherence metrics, to healthcare providers for adjusting a medication regimen of the first medication relative to the first biological system.

12. The telemetric control system of claim 1, wherein telemetric control system comprises:

a first activatable member of the at least one activatable member which is activatable to track the first medication, a second activatable member of the at least one activatable member which is activatable to track the second medication, and a third activatable member of the at least one activatable member which is activatable to track a third medication.

13. The telemetric control system of claim 1, wherein the powering mechanism comprises a rechargeable lithium-ion battery with USB charging via a USB-A or micro-USB port, including a power management module that regulates charging cycles and optimize energy distribution for low-power operations between actuations of the at least one activatable member.

14. The telemetric control system of claim 1, wherein the powering mechanism comprises a USB-C port supporting Power Delivery (PD) standards for faster charging and simultaneous data transfer during firmware updates or EHR synchronization.

15. The telemetric control system of claim 1, wherein the disposable battery system of the powering mechanism comprises one of a coin-cell or alkaline battery, coin cel or alkaline battery being housed in an accessible compartment of the telemetric control system and optimized for ultra-low power consumption through power saving modes that deactivate non-essential components from drawing energy from the powering mechanism during non-medication delivery times associated with the first medication.

16. The telemetric control system of claim 1, wherein the wireless charging energy system of the powering mechanism comprises wireless charging via a Qi-standard inductive charging with an embedded coil, allowing cable-free energy transfer to the telemetric control system and supporting sealed, water-resistant designs of the telemetric control system for enhanced durability in clinical or non-critical environments.

17. The telemetric control system of claim 1, the energy harvesting system is configured to generate energy for the telemetric control system based on one or more:

a piezoelectric generator embedded in the at least one activatable member, such that the piezoelectric generator converts mechanical energy from actuations of the at least one activatable member into electrical energy that powers the telemetric control system, or a photovoltaic cell for capturing and converting ambient light into electrical energy that powers the telemetric control system.

18. The telemetric control system of claim 1, wherein the powering mechanism comprises a hybrid system with a primary rechargeable battery and a secondary disposable battery for failover, the control logic being configured to monitor battery levels and switching energy sources to maintain uninterrupted operation of the telemetric control system during power disruptions.

19. The telemetric control system of claim 1, wherein the telemetric control system is configured for interoperability with Internet of Things (IoT) ecosystems, such that the signal transmitter communicates with external devices to contextualize dosage decisions based on environmental data, and blockchain technology for immutable logging of actuation events to ensure tamper-proof audit trails.

20. The telemetric control system of claim 1, wherein the at least one wireless network is selected from a group consisting a Bluetooth Low Energy (BTLE) network, a Wi-Fi network, a satellite communications network, or a cellular network.

* * * * *